(12) United States Patent
Reimels

(10) Patent No.: US 8,702,756 B2
(45) Date of Patent: Apr. 22, 2014

(54) CLAMPING INTERSPINOUS SPACER APPARATUS AND METHODS OF USE

(75) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 125 days.

(21) Appl. No.: 13/240,846

(22) Filed: Sep. 22, 2011

(65) Prior Publication Data

US 2012/0078302 A1    Mar. 29, 2012

Related U.S. Application Data

(60) Provisional application No. 61/385,800, filed on Sep. 23, 2010.

(51) Int. Cl.
*A61B 17/70*    (2006.01)
(52) U.S. Cl.
USPC .......................................... 606/248; 606/249
(58) Field of Classification Search
USPC ............... 606/246, 248, 249, 59, 247, 277; 623/17.11, 17.16; 403/233–236, 374.3; 24/514, 529, 569
See application file for complete search history.

(56) References Cited

U.S. PATENT DOCUMENTS

| | | | | |
|---|---|---|---|---|
| 1,977,725 A | * | 10/1934 | Heidbrink | 248/129 |
| 3,512,380 A | * | 5/1970 | Winter | 70/19 |
| 4,901,964 A | * | 2/1990 | McConnell | 248/231.51 |
| 7,017,238 B2 | * | 3/2006 | Messina | 24/279 |
| 2006/0271049 A1 | * | 11/2006 | Zucherman et al. | 606/61 |
| 2007/0032790 A1 | * | 2/2007 | Aschmann et al. | 606/61 |
| 2007/0093825 A1 | | 4/2007 | Ferree et al. | |
| 2008/0114456 A1 | * | 5/2008 | Dewey et al. | 623/17.16 |
| 2008/0147190 A1 | * | 6/2008 | Dewey et al. | 623/17.16 |
| 2008/0177306 A1 | * | 7/2008 | Lamborne et al. | 606/246 |
| 2008/0183211 A1 | | 7/2008 | Lamborne et al. | |
| 2009/0054988 A1 | * | 2/2009 | Hess | 623/17.16 |
| 2009/0138046 A1 | | 5/2009 | Altarac et al. | |
| 2009/0259316 A1 | | 10/2009 | Ginn et al. | |
| 2009/0292316 A1 | * | 11/2009 | Hess | 606/249 |
| 2011/0046674 A1 | * | 2/2011 | Calvosa et al. | 606/249 |
| 2011/0066186 A1 | * | 3/2011 | Boyer et al. | 606/249 |
| 2013/0066374 A1 | * | 3/2013 | Galley et al. | 606/249 |
| 2013/0231704 A1 | * | 9/2013 | Larroque-Lahitette | 606/277 |

* cited by examiner

*Primary Examiner* — Jan Christopher Merene
(74) *Attorney, Agent, or Firm* — Michael J. Loi

(57) ABSTRACT

An interspinous process spacer includes a main body, a first wing, and a screw. The main body includes a first securing member extending from a top portion of the main body that engages a first vertebra and a bottom portion of the main body that engages a second vertebra. The first wing pivotably couples to a distal portion of the main body and includes a second securing member extending parallel to the first securing member to form a first clamp. The screw is positionable within the main body and includes a distal end that positions the first wing between a first position and a second position. The first clamp includes a first diameter in the first position and a second diameter in the second position.

6 Claims, 9 Drawing Sheets

CLAMPING INTERSPINOUS SPACER APPARATUS AND METHODS OF USE

CROSS-REFERENCE TO RELATED APPLICATIONS

This application claims priority to U.S. Provisional Patent Application No. 61/385,800, filed Sep. 23, 2010, which is incorporated herein by reference.

FIELD

The present invention relates to the field of interspinous devices, and more particularly, relates to an interspinous apparatus inserted between two spinous processes of the lumbar spine.

BACKGROUND

Lumbar Spinal Stenosis (LSS) is one of the most common reasons for spine surgery in older people. Spinal stenosis is a medical condition in which the spinal canal narrows and compresses the spinal cord and nerves. This is usually due to the natural process of spinal degeneration that occurs with aging. It may also be caused by spinal disc herniation, osteoporosis, or a tumor. Spinal stenosis may affect the cervical or lumbar vertebrae or both. Lumbar spinal stenosis results in lower back pain as well as pain or abnormal sensations in the legs, thighs, feet or buttocks, or loss of bladder and bowel control.

Laminectomy is a basic part of the surgical treatment of LSS and is an effective remedy for severe spinal stenosis. Laminectomy can be done without spinal fusion; however, if the spinal column is unstable, fusion may be required for the laminectomy.

Lumbar interspinous process decompression ("IPD"), also known as interspinous distraction or posterior spinal distraction, has been proposed as a minimally invasive alternative to laminectomy and fusion. In IPD, an interspinous distraction implant, also called a spacer, is inserted between the spinous processes through a small (4-8 cm) incision. The supraspinous ligament is maintained and assists in holding the implant in place, such that no laminotomy, laminectomy, or foraminotomy is performed. The device is intended to restrict painful motion while enabling otherwise normal motion. The device theoretically enlarges the neural foramen, decompresses the cauda equina, and acts as a spacer between the spinous processes to maintain the flexion of the spinal interspace.

Therefore, a device that can be implanted between two spinous processes of the spine more easily and which involves less invasive procedures than present day procedures is needed. Also, a device which can easily be adapted for both fusion and non-fusion procedures is needed. Such a device would aid in the treatment for spinal stenosis. Current prior art devices are made of multiple parts, are bulky, and require complex delivery instrumentations to position, assemble and deploy a clamping apparatus. The present invention attempts to solve these problems, as well as others.

SUMMARY OF THE INVENTION

Provided herein are systems, methods and apparatuses for a clamping interspinous spacer. An interspinous process spacer includes a main body, a first wing, and a screw. The main body includes a first securing member extending from a top portion of the main body that engages a first vertebra and a bottom portion of the main body that engages a second vertebra. The first wing pivotably couples to a distal portion of the main body and includes a second securing member extending parallel to the first securing member to form a first clamp. The screw is positionable within the main body and includes a distal end that positions the first wing between a first position and a second position. The first clamp includes a first diameter in the first position and a second diameter in the second position.

In other features, the distal end of the screw includes a curved portion that engages a curved section of the first wing and the proximal end of the screw includes a threaded portion that engages a threaded bore in the main body. The screw advances towards the distal portion to position the first wing from the first position to the second position. The first diameter is greater than a thickness of a spinous process of the first vertebra and the second diameter is less than the first diameter. The first wing pivotably couples to the main body by one of a living hinge and a fixed axis of rotation.

In still other features, the interspinous process spacer further includes a third securing extending from the bottom portion of the main body that engages the second vertebra and a second wing pivotably coupled to a proximal portion of the main body and including a fourth securing member extending parallel to the third securing member to form second clamp. The screw includes a proximal end that positions the second wing between a first position and a second position. The second clamp includes a first diameter in the first position and a second diameter in the second position.

In other features, the distal end of the screw includes a curved portion that engages a curved section of the first wing and the proximal end of the screw includes a threaded portion that engages a threaded bore in the second wing. The distal end of the screw advances towards the distal portion to position the first wing from the first position to the second position and the proximal end of the screw rotates within the proximal portion to position the second wing from the first position to the second position. The first diameters are greater than thicknesses of spinous processes of the first and second vertebrae respectively and the second diameters are less than the first diameters. The first and second wings pivotably couple to the main body by one of a living hinge and a fixed axis of rotation.

In various embodiments, the interspinous process spacer generally comprises a main body, a clamp section, and a slot, wherein the main body includes a distal portion, a proximal portion, a top portion, and a bottom portion; the distal portion includes a first wing and the proximal portion includes a second wing, the bottom portion includes a curved segment, top portion includes the clamp section, wherein the clamp section includes a first clamp and a second clamp; the first wing operably coupled to the slot and the first clamp, wherein the slot generally extends along the transverse axis of the main body; the slot includes a slot opening located at or near the bottom portion and a slot curvature at or near the top portion; and the clamp section and the curved segment enable the interspinous spacer to be secured between two spinous processes such that one spinous process rests in the curved segment and another spinous process rests in the clamp section.

The systems, methods, and apparatuses are set forth in part in the description which follows, and in part will be obvious from the description, or can be learned by practice of the methods, apparatuses, and systems. The advantages of the methods, apparatuses, and systems will be realized and attained by means of the elements and combinations particularly pointed out in the appended claims. It is to be understood that both the foregoing general description and the following detailed description are exemplary and explanatory only and are not restrictive of the systems, methods, and apparatuses, as claimed.

BRIEF DESCRIPTION OF THE DRAWINGS

The foregoing and other features and advantages of the invention are apparent from the following detailed description of exemplary embodiments, read in conjunction with the accompanying drawings. The detailed description and drawings are merely illustrative of the invention rather than limiting, the scope of the invention being defined by the appended claims and equivalents thereof.

DETAILED DESCRIPTION OF THE INVENTION

Figure 1:
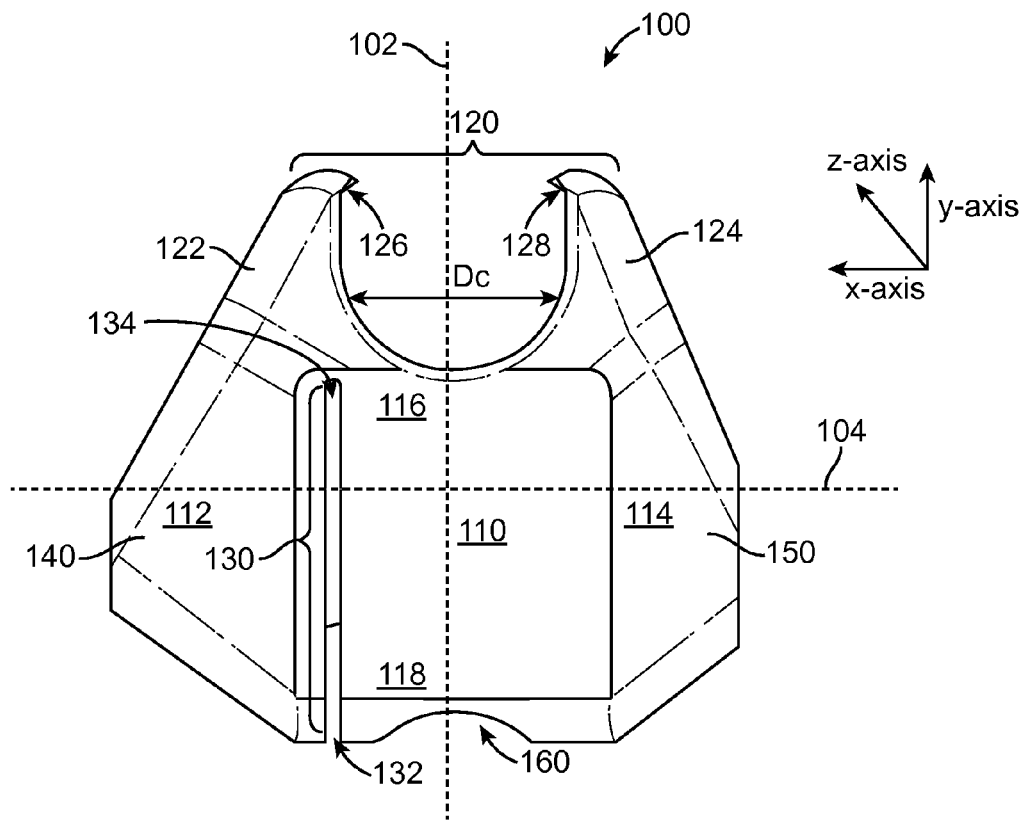
FIG. 1 is a perspective side view of the exterior portion for one embodiment of the clamping interspinous spacer.

In the accompanying figures, like elements are identified by like reference numerals among the several preferred embodiments of the present invention.

Generally speaking, the clamping interspinous spacer 100 comprises a main body 110, a clamp section 120, and a slot 130, as shown in FIG. 1. The main body 110 provides interspinous distraction of the spinous process when implanted between adjacent spinous processes, while the clamp section 120 and the slot 130 operate to clamp or secure the main body 110 between adjacent spinous processes. The main body 110 includes a distal portion 112, a proximal portion 114, a top portion 116, and a bottom portion 118. The clamping interspinous spacer 100 includes a transverse axis 102, generally shown along the y-axis and along the proximal portion 114 and the distal portion 112. The clamping interspinous spacer 100 includes a longitudinal axis 104, which is generally shown along the x-axis and along the top portion 116 and the bottom portion 118. The clamping interspinous spacer 100 includes a thickness generally along the z-axis, which may approximate the thickness of a spinous process. The distal portion 112 includes a first wing 140 and the proximal portion 114 includes a second wing 150. The bottom portion 118 includes a curved segment 160, which is immovable relative to the second wing 150. The top portion 116 includes the clamp section 120 that is operably coupled to the first wing 140, wherein the clamp section 120 includes a first clamp 122 and a second clamp 124. The clamp section 120 includes a diameter Dc between the first clamp 122 and the second clamp 124. The first clamp 122 and the second clamp 124 may include inward facing hooks or clasps 126 and 128 on the distal end of the clamps 122 and 124, respectively. The hooks 126 and 128 may include sharp edges that act to secure the first clamp and second clamp 122 and 124 to outer portions or bony edges of the spinous process.

As shown in FIG. 1, the first wing 140 is operably coupled to the slot 130 and the first clamp 122. The slot 130 includes a length that generally extends from about the top portion 116 to the bottom portion 118, while the slot 130 generally extends along the longitudinal axis 102 of the main body 110, generally shown in the y-direction. The slot 130 includes a slot opening 132 located at or near the bottom portion 118 and a slot curvature 134 at or near the top portion 116. The slot curvature 134 acts as a pivot point to close and tighten the clamp section 120 when the slot 130 is displaced or angulated. The slot 130, the clamp section 120, and the curved segment 160 secure the clamping interspinous spacer 100 between two spinous processes that rest in the curved segment 160 and the clamp section 120. The main body 110 provides distraction of the spinous process when implanted between adjacent spinous processes by way of a cam action to restore original spinal column height when the main body 110 is rotated about the longitudinal axis 104.

As shown in FIG. 1, the main body 110 includes a rectangular x-section on the exterior portion of the main body 110 that provides for a sleek exterior to be passed through soft tissue with minimal trauma. However, the exterior portion of the main body 110 may include alternative shaped-sections that are angled on the periphery of the exterior, such as v-sections, square, oval, or elliptical shapes in other embodiments. The exterior portion of the main body 110 may be flat on the central portion with curved-in outer sides in one embodiment. The first wing 140 and the second wing 150 may generally be in a trapezoidal shape in one embodiment; however, the first wing 140 and the second wing 150 may assume any generally polygonal, triangular, or hexagonal shape in alternative embodiments. The clamp section 120 may generally be in a U-shape, or a C-shape in one embodiment; however, the clamp section 120 may assume alternative shapes such as to conform to the spinous process, such as V-shaped, cup-shaped, and the like. The clamp section 120 may clamp down and secure the clamping interspinous spacer onto any spinous process on the vertebrae, including, but not limited to, the cervical, thoracic, lumbar, or sacral sections of the vertebrae.

Figure 2:
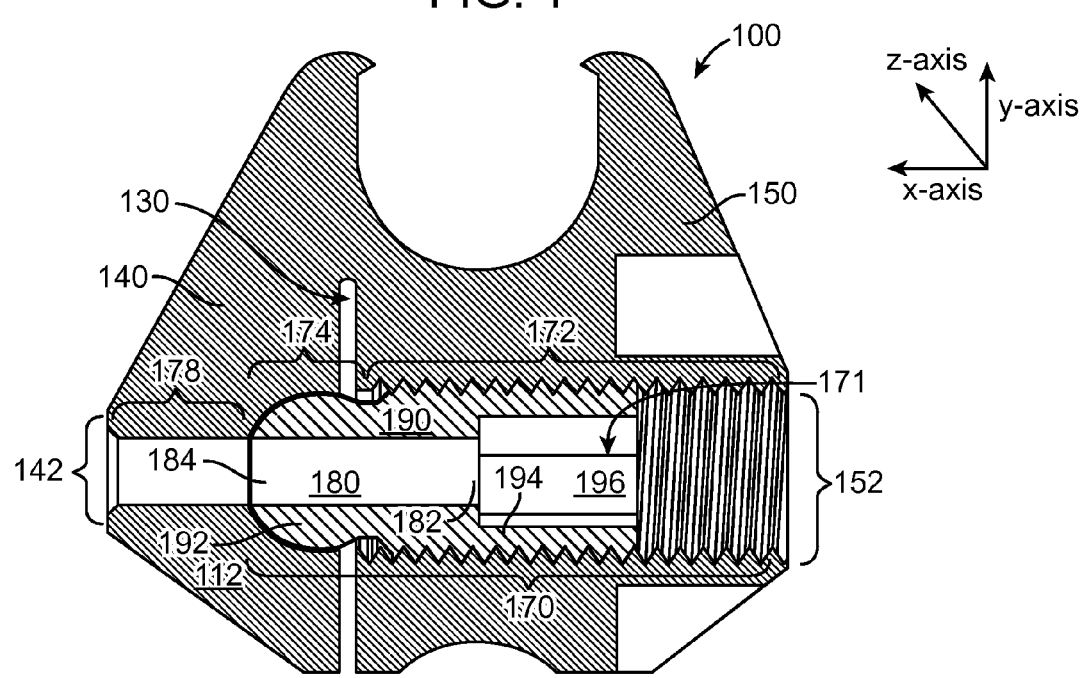
FIG. 2 is a cross-sectional view of one embodiment of the clamping interspinous spacer showing the central screw 190 within the central longitudinal lumen and the acceptor position and the screw tube lumen within the central screw 190.

As shown in FIG. 2, the main body 110 includes a central longitudinal lumen 170 extending along at least a portion of the longitudinal axis of the main body 110, generally shown in the x-axis direction in FIG. 2. The central longitudinal lumen 170 includes a threaded section 172, a curved section 174 and a distal lumen 178. The lumen 170 may receive a central screw 190. The threaded section 172 extends from the proximal portion 114 and through the central portion of the main body 110 to the slot 130. The threaded section 172 includes an opening 152 on the proximal portion 114 of the second wing 150. The opening 152 is shaped to allow the central screw 190 to operably couple to the threaded section 172. The curved section 174 longitudinally extends from the slot 130 towards the distal portion 112 and the first wing 140. The slot 130 may be generally perpendicular to the central screw 190; however, the slot 130 may be at an angle in relation to the central screw 190. The central screw 190 includes a distal curved section 192, a central threaded portion 194, and a screw lumen 171 positioned coaxially within the central screw 190. The distal curved section 192 operably engages the curved section 174 of the first wing 140, such as to abut the curved section 174 and support the first wing 140 during delivery and displace the first wing 140 during longitudinal movement of the central screw 190. The curved section 174 and the distal curved section 192 are fitted to a particular curvature in order for the first wing to deform along the longitudinal and transverse axis. The central threaded portion 194 operably engages the threaded section 172 by a threading in a screw-like fashion. Preferably, the distal curved section 192 includes a smaller diameter than the central threaded portion 194, such that the central screw 190 may rotatably engage with the threaded portion 172 of the central longitudinal lumen 170. The screw lumen 171 is located concentrically within the central screw 190 and includes a proximal acceptor position 196 and a central tube lumen 180, which are both coaxially positioned within the central screw 190. The distal acceptor position 196 is shaped to fit a screwdriver, preferably a hexagonal screwdriver in one embodiment. The central tube lumen 180 includes a proximal end 182 and a distal end 184. The distal end 184 is operably coupled to the distal lumen 178, where the distal lumen 178 is included within the first wing 140. The distal lumen 178 includes an opening 142 on the distal portion 112. The central tube lumen 180 and the distal lumen 178 longitudinally extend from the acceptor position 196 to the opening 142 of the distal section 112, such that a guide wire (not shown) may longitudinally extend through the central longitudinal lumen 170 of the clamping interspinous spacer 100 for placement between adjacent spinous processes.

Figure 3:
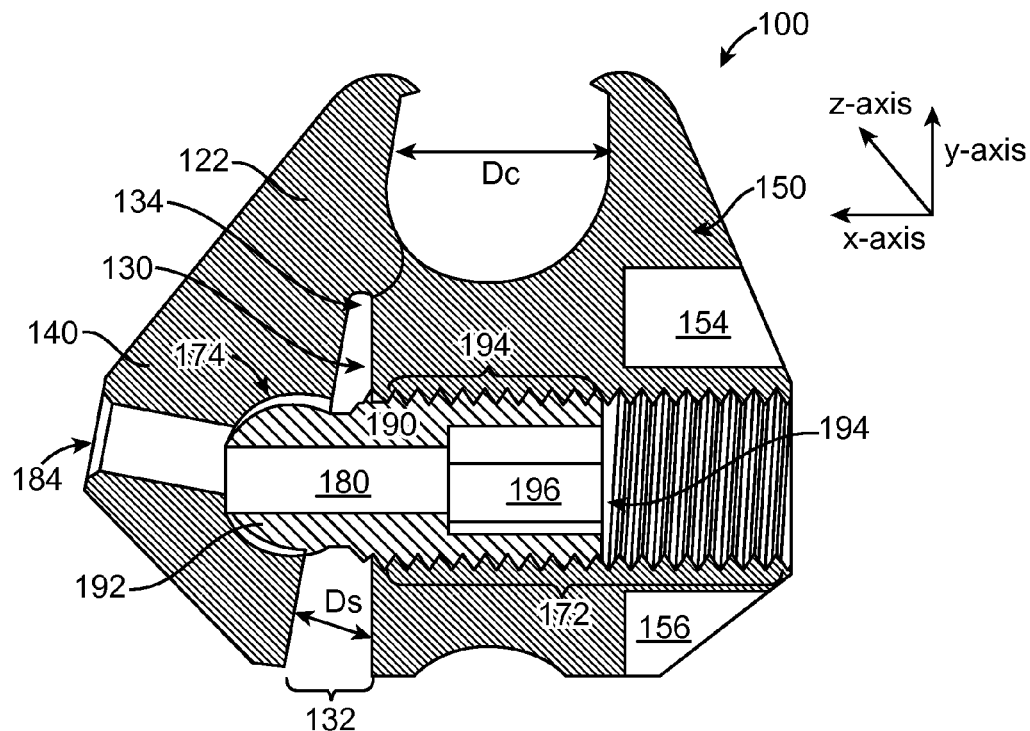
FIG. 3 is a cross-sectional view of one embodiment of the clamping interspinous spacer showing the central screw 190 longitudinally displacing the first wing 140.

The central threaded portion 194 of the central screw 190 concentrically engages the threaded section 172 to become longitudinally movable by way of rotating the central screw 190 by an operator, as shown in FIG. 3. Upon rotation of the central screw 190, the distal curved section 192 then proceeds to push or deform the first wing 140 by pushing the curved section 174 along the longitudinal axis and the transverse axis, which subsequently deforms the first wing 140 along the longitudinal and transverse axis and displaces the clamp 122 to tighten the clamp portion 120 onto a spinous process (not shown). The tightening of the clamp portion 120 decreases the diameter Dc proportional to the distance of the slot opening 132 and increases the diameter Ds of the slot 130. The diameters Dc and Ds may include a maximum and a minimum at which they may increase and/or decrease. The slot curvature 134 acts as a pivot point to allow the first clamp 122 and the clamp portion 120 to deform and angulate onto the spinous process. Alternatively, the slot curvature 134 includes a hinge that is coupled with the first clamp 122, the first wing 140, and the top portion 116 of the main body. The hinge is a type of bearing that connects the first clamp 122 and the first wing 140 with the top portion 116 of the main body and allows only a limited angle of rotation between them. As such, the first clamp 122 and the first wing 140 connected by the hinge rotate relative to the top portion 116 of the main body 110 about a fixed axis of rotation. The hinge may be made of flexible material such as a polymer or Nitinol, titanium, and the like to allow for super elastic or plastic deformation.

Figure 4:
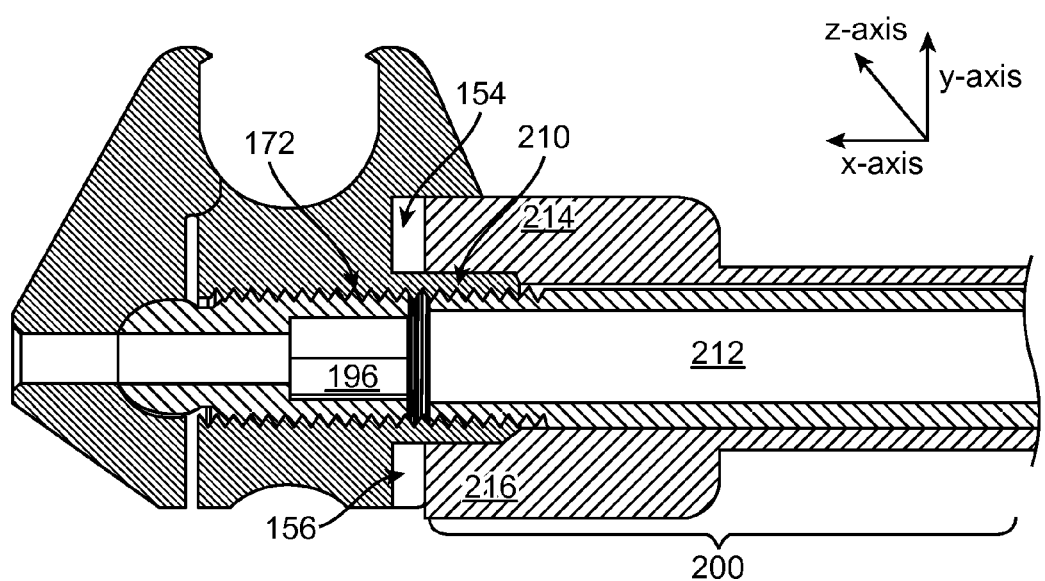
FIG. 4 is a cross-sectional view of one embodiment of the clamping interspinous spacer showing the delivery position with the cannulated threaded rod 200 engaging the proximal end of the clamping interspinous spacer.

As shown in FIG. 4, the second wing 150 includes a first lumen 154 and a second lumen 156, such as to receive a cannulated rod 200 and to permit a screw driver to pass through a cannula 212 located coaxially within the cannulated rod 200. The cannulated threaded rod 200 operably engages the proximal end of the threaded section 172 as to abut the acceptor position 196. The cannulated threaded rod 200 includes a distal threaded section 210 to concentrically engage the threaded section 172 and the proximal section 114 of the main body. The cannula 212 also passes through the opening 152. The cannulated threaded rod 200 includes a top flange 214 and a bottom flange 216 to concentrically seat and secure the cannulated thread rod 200 into the first lumen 154 and the second lumen 156 of the second wing 150.

Figure 5:
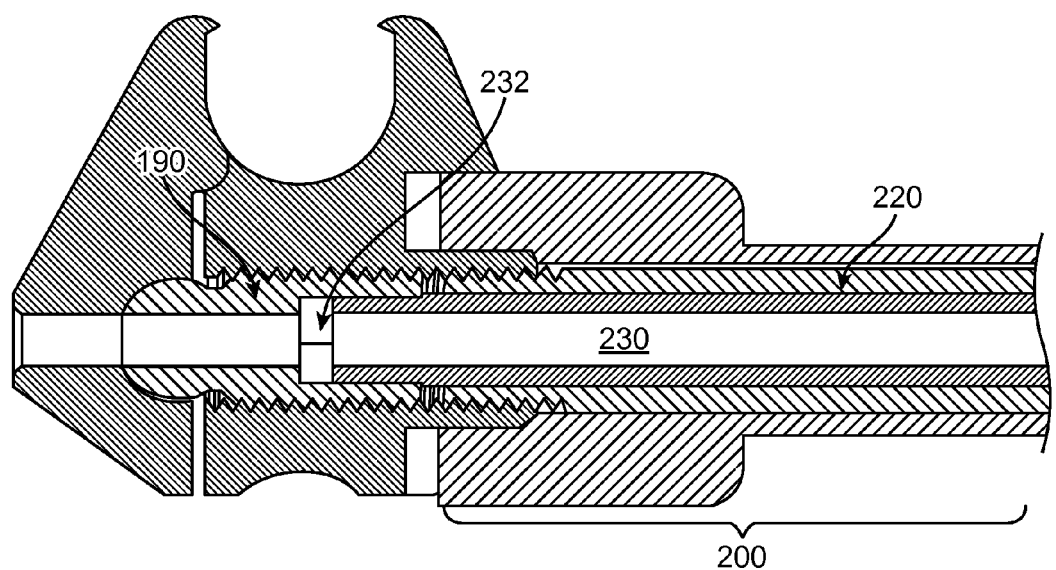
FIG. 5 is a cross-sectional view of one embodiment of the clamping interspinous spacer showing the cannulated threaded rod 200 and the hex driver 230 inside the lumen 220 of the cannulated threaded rod 200 to operably engage the inner surface of the central screw 190.
Figure 7A:
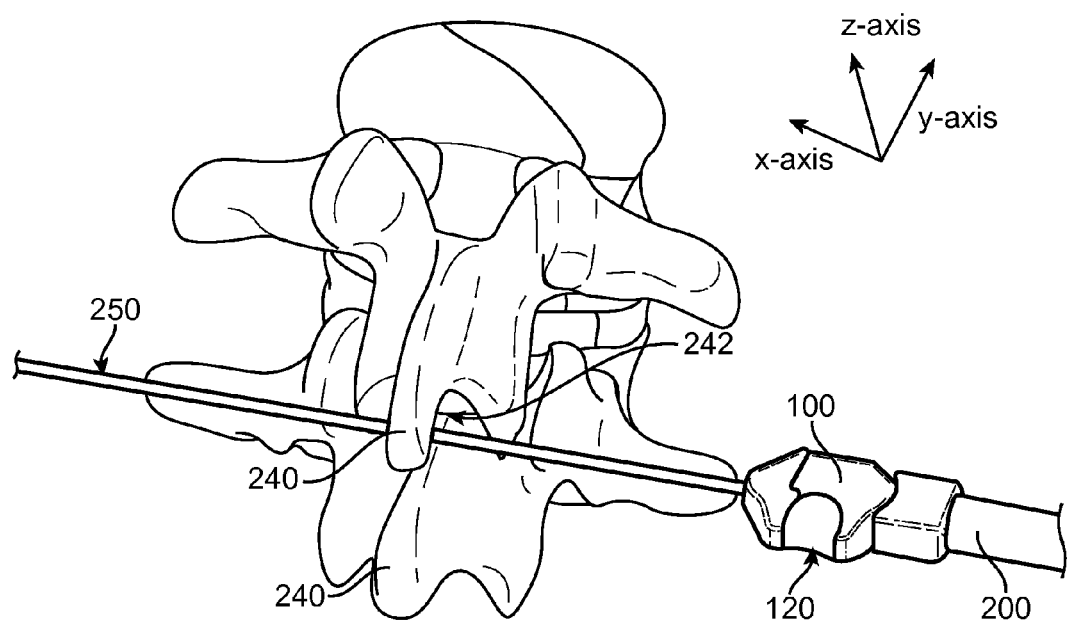
FIG. 7A is a perspective view of the spinous processes 240 and the interspinous location 242 whereby a guide wire is delivered with the interspinous spacer.
Figure 7B:
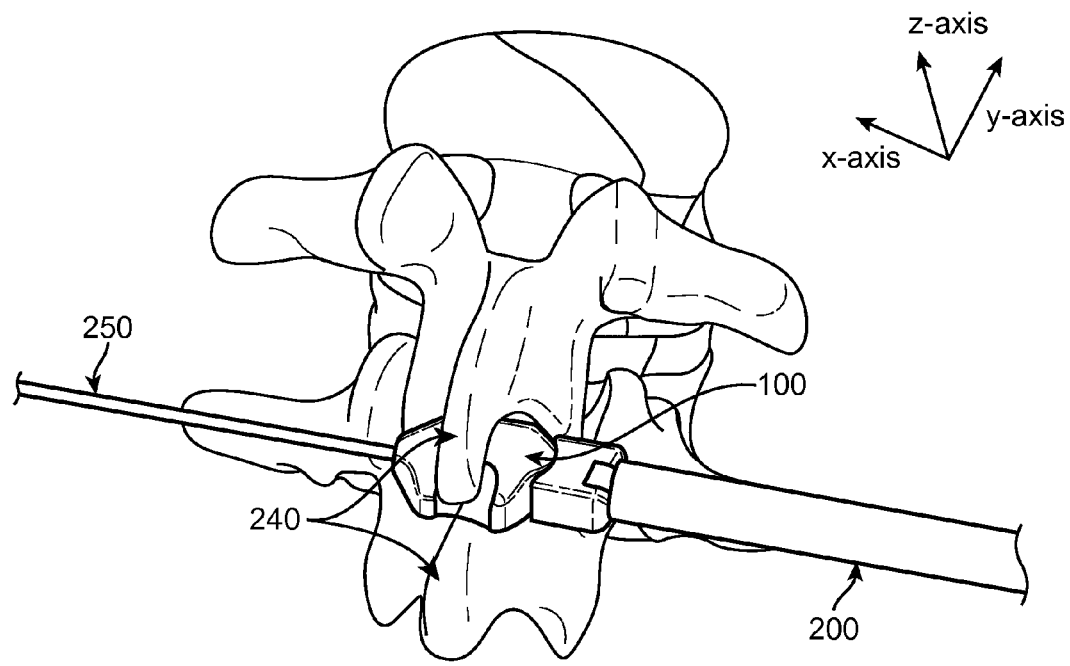
FIG. 7B is a perspective view of the spinous processes 240 whereby the interspinous spacer is placed between adjacent spinous processes at a 90 degree angle with respect to the z-axis.
Figure 7C:
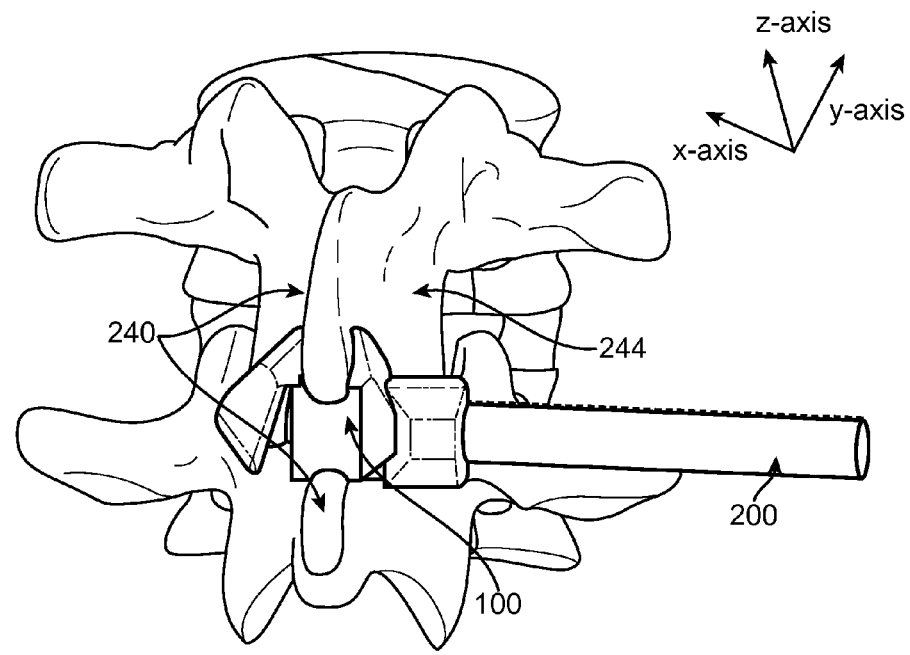
FIG. 7C is a perspective view of the interspinous spacer rotated 90 degrees.

During delivery, the clamping interspinous spacer 100 is delivered over a guide wire 250 or kirschner wire ("k-wire") to an interspinous location 242, generally shown in FIG. 7A. The clamping interspinous spacer 100 is placed between adjacent spinous processes 240 with the cannulated threaded rod 200, whereby the clamp section 120 is pointing towards the z-axis or away from the spine of the patient. Once the clamping interspinous spacer 100 is between adjacent spinous processes 240, as shown in FIG. 7B, the clamping interspinous spacer 100 is rotated 90 degrees by the cannulated threaded rod 200 towards the y-axis or upwards towards the patient's head or feet in the y-axis direction, which provides a cam action to distend the vertebral bodies 244 and place the clamp section 120 around the spinous process, as shown in FIG. 7C. Once the clamp section 120 is around the spinous process a hex driver 230 is slid inside a lumen 220 of the cannulated threaded rod 200, whereby the hex driver 230 operably engages the inner surface of the acceptor position 196 in the central screw 190 (not shown) with a hexagonal screw portion 232, as shown in FIG. 5.

Figure 6:
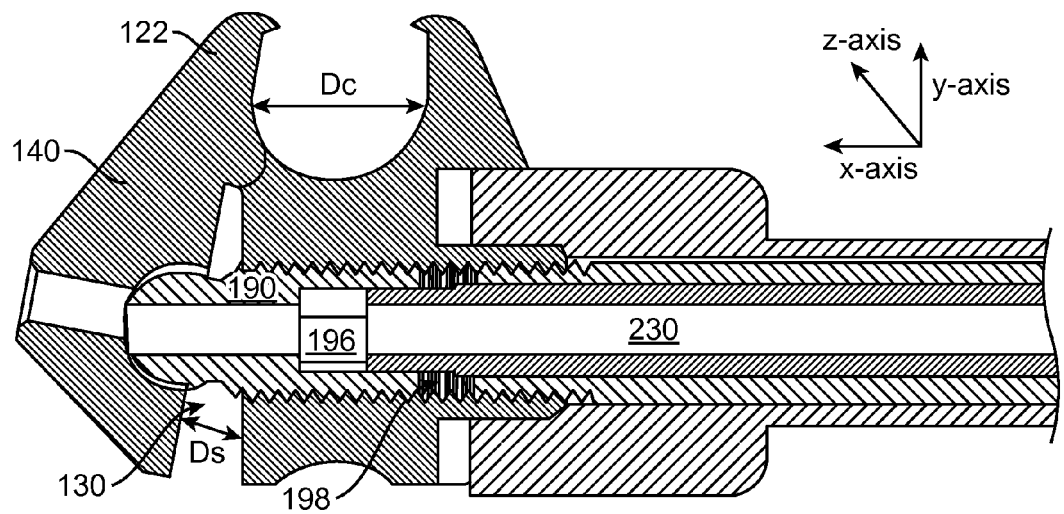
FIG. 6 is a cross-sectional view of one embodiment of the clamping interspinous spacer with the cannulated threaded rod 200 and the hex driver 230 operably engaged with the acceptor position 190.
Figure 7D:
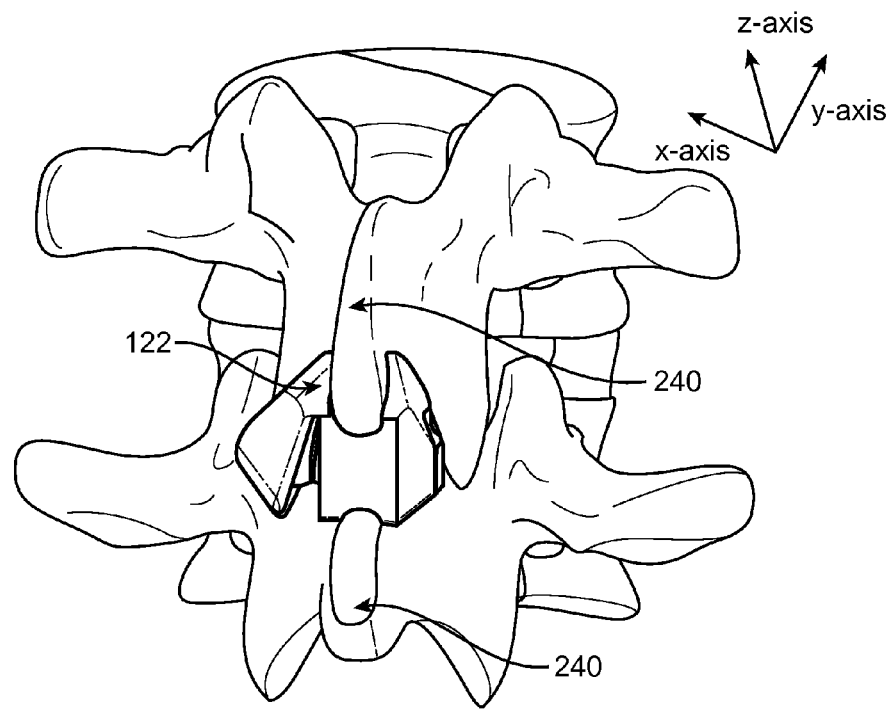
FIG. 7D is a perspective view of the interspinous spacer deployed and clamped onto the spinous process.

As shown in FIG. 6, the central screw 190 is operably coupled with the hex driver 230 by way of the acceptor position 196, whereby an operator rotates the hex driver 230 to rotate the central screw 190 and longitudinally advance the central screw 190 towards the distal portion 112, and increasing the diameter Ds of the slot 130. The longitudinal displacement of the central screw 190 causes the first wing 140 to deform and thereby deform the first clamp 122, which decreases the diameter Dc. The first clamp 122 clamps and tightens against the spinous process 240 to provide increase stabilization for the spinal spacer and maintain distraction of two spinous processes 240, generally shown in FIG. 7D.

In one embodiment, the central screw 190 may be coupled with a locking mechanism 198 as to prevent the backward movement of the central screw 190, which would decrease the diameter Ds and increase diameter Dc, as shown in FIG. 6. The locking mechanism 198 may be behind the central screw 190, which either may be a threaded ring or the threaded portion 172 of the central lumen 170. The threaded ring may be rotated in the central lumen 170 after the central screw 190 has deformed the first wing 140 and the first clamp 122. The threaded portion 172 may include a threaded lock portion that maintains the central screw 190 from displacing longitudinally backwards once the first wing 140 and the first clamp 122 is deformed and engaged on the spinous process.

Figure 8:
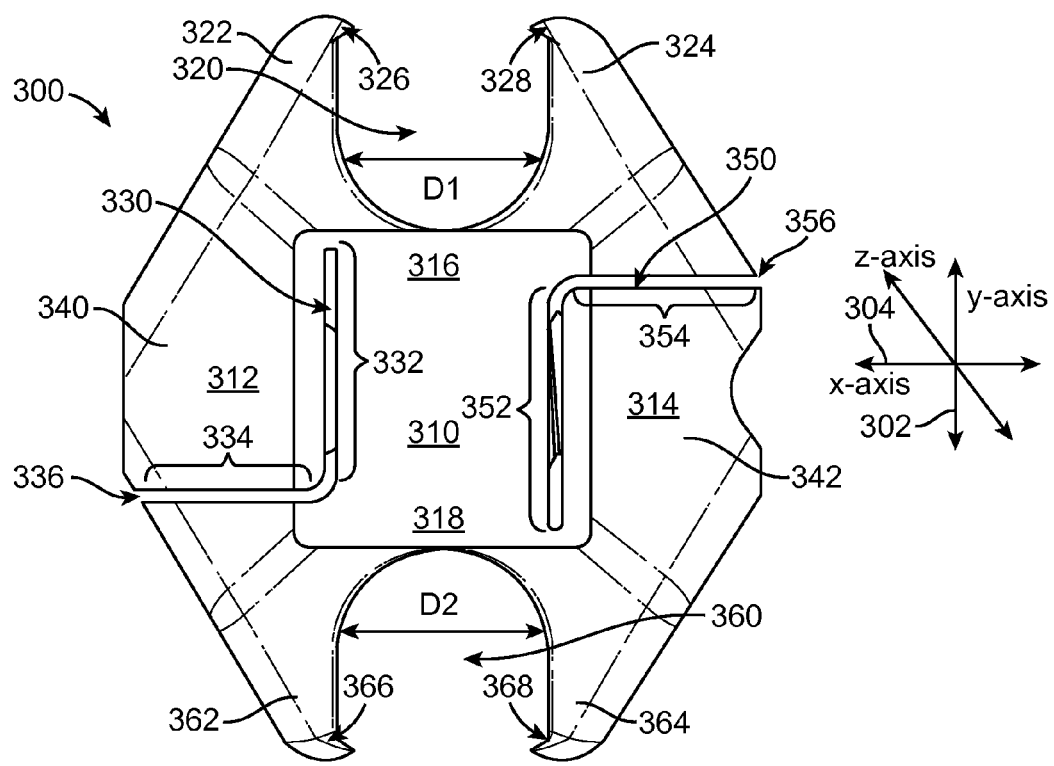
FIG. 8 is a perspective view of the exterior portion for one embodiment of the bilateral interspinous spacer.

In an alternative embodiment, the interspinous spacer is shown in a bilateral configuration 300. The bilateral interspinous spacer 300 comprises a main body 310, a first clamp section 320, a second clamp section 360, a first slot 330, and a second slot 350, as shown in FIG. 8. The main body 310 provides interspinous distraction of the spinous process when implanted between adjacent spinous processes, while the first and second clamp sections 320 and 360 and first and second slots 330 and 350, respectively, and operate to clamp or secure the main body 310 between adjacent spinous processes. The central body 310 includes a distal portion 312, a proximal portion 314, a top portion 316, and a bottom portion 318. The bilateral interspinous spacer 300 includes a longitudinal axis 304, generally shown along the x-axis with the proximal portion 314 and the distal portion 312. The bilateral interspinous spacer 300 includes a transverse axis 302, which is generally shown along the y-axis with the top portion 316 and the bottom portion 318. The distal portion 312 includes a first wing 340 and the proximal portion 314 includes a second wing 342. The bottom portion 318 includes the second clamp section 360, wherein the second clamp section 360 includes a first clamp 362 and a second clamp 364. The top portion 316 includes the first clamp section 320, wherein the first clamp section 320 includes a first clamp 322 and a second clamp 324. The first clamp section 320 includes a first diameter D1 and the first clamp 322 and the second clamp 324 may include inward facing hooks or clasps 326 and 328 on the distal end of the clamps 322 and 324, respectively. The second clamp section 360 includes a second diameter D2 and the first clamp 362 and the second clamp 364 may include inward facing hooks or clasps 366 and 368 on the distal end of the first and second clamps 362 and 364, respectively. The hooks 366 and 368 may include sharp edges that act to secure the first clamp and second clamp 122 and 124 to outer portions or bony edges of the spinous process.

As shown in FIG. 8, the first wing 340 is operably coupled to the first slot 330 and the first clamp 322. The second wing 342 is operably coupled to the second slot 350 and the second clamp 364. The first slot 330 generally comprises a first leg 332 and a second leg 334 in an L-shape, where the first leg 332 extends along the transverse axis of the main body 310 and the second leg 334 extends along the longitudinal axis of the main body 310. The transverse axis is generally shown in the y-direction and the longitudinal axis is generally shown in the x-direction. The first and second leg 332 and 334 may be perpendicular with respect to each other; however, the first and second leg 332 and 334 may at an angle greater or less than 90 degrees with respect to each other. The angle with respect to the first and second leg 332 and 334 may be selected as to permit the first wing 340 to deform at a particular angle or distance. The second slot 350 generally comprises a first leg 352 and a second leg 354 in an L-shape, where the first leg 352 extends along the transverse axis of the main body 310 and the second leg 354 extends along the longitudinal axis of the main body 310. The first and second leg 352 and 354 may be perpendicular with respect to each other; however, the first and second leg 352 and 354 may at an angle greater or less than 90 degrees with respect to each other. The first and second slots 330 and 350 are shaped as to allow the first and second wings 340 and 342 to deform, respectively. The first and second slots 330 and 350 may generally alternative shapes, such as V-shaped, C-shaped, and the like.

As shown in FIG. 8, the first slot 330 includes a slot opening 336 located at or near the distal portion 312 and the second slot 350 includes a slot opening 356 at or near the proximal portion 314. The first clamp section 320 and the second clamp section 360 enable the bilateral clamping interspinous spacer 300 to be secured between two adjacent spinous processes, such that one spinous process rests in the first clamp section 320 and a second spinous process rests in the second clamp section 360. The second leg 334 extends from the middle section of the main body to the exterior edge of the distal portion 312, while the second leg 356 extends from the middle section of the main body to the exterior edge of the proximal portion 314. In one embodiment, the main body 310 includes a rectangular cross-section on the exterior portion of the main body 310; however, the exterior portion of the main body 110 may include alternative sections, such as v-sections, square, oval, or elliptical shapes. The exterior portion of the main body 310 may be flat on the central portion with proximal and distal sides curved-in towards the interior of the main body 310. The first wing 340 and the second wing 342 may generally be in a trapezoidal shape; however, the first wing 340 and the second wing 342 may assume any generally polygonal, triangular, or hexagonal shape. The first clamp section 320 and the second clamp section 360 may generally be in a U-shape or C-shape in one embodiment; however, the clamp sections 320 and 360 may assume alternative shapes such as to conform to the spinous process, such as V-shaped, cup-shaped, and the like.

Figure 9:
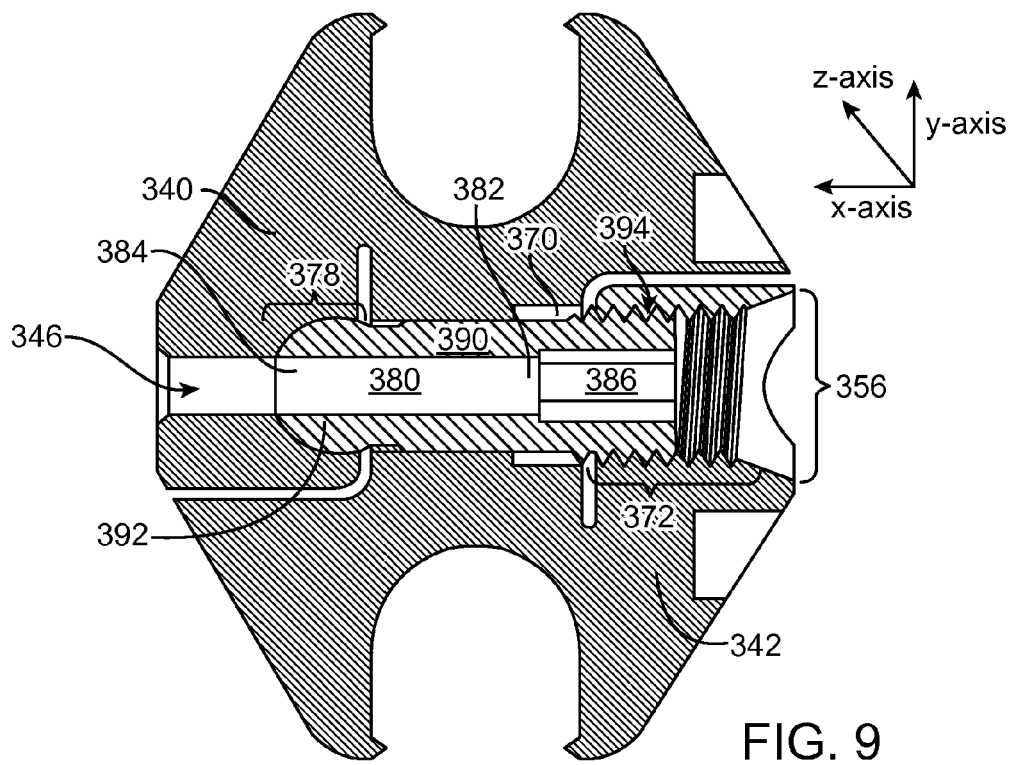
FIG. 9 is a cross-sectional view of one embodiment of the bilateral interspinous spacer showing the central screw 390 within the central longitudinal lumen and the acceptor position 386 and the screw tube lumen 380 within the central screw 390.

As shown in FIG. 9, the main body 310 includes a central longitudinal lumen 370 extending along at least a portion of the longitudinal axis of the central body 310, generally shown in the x-axis direction in FIG. 9. The central longitudinal lumen 370 includes a threaded section 372, a curved section 378, and a wing lumen 346. A central screw 390 is coaxially engaged within the central longitudinal lumen 370 from the threaded section 372 to the curved section 378. The threaded section 372 extends from the proximal portion 314 and through the second wing 342. The threaded section 372 includes an opening 356, which is included in the proximal portion 114 of the second wing 342. The curved section 378 longitudinally extends from the first slot 330 to the distal portion 312 and in the first wing 340.

As shown in FIG. 9, the central screw 390 includes a central tube 380, which is a tubular opening coaxially within the central screw 390 with a proximal end 382 and a distal end 384. The first wing 340 includes the wing lumen 346 to operably couple the distal end 384 of the central tube 380 and form a contiguous lumen therebetween. The central screw 390 includes a distal curved portion 392, a screw acceptor portion 386, and a threaded proximal portion 394. The central tube 380 longitudinally extends from the screw acceptor portion 386 to the distal portion 392 of the central screw 190. The screw acceptor portion 386 extends to the proximal portion of the central screw 390 to accept a screw like or hexagonal screw device.

Figure 10:
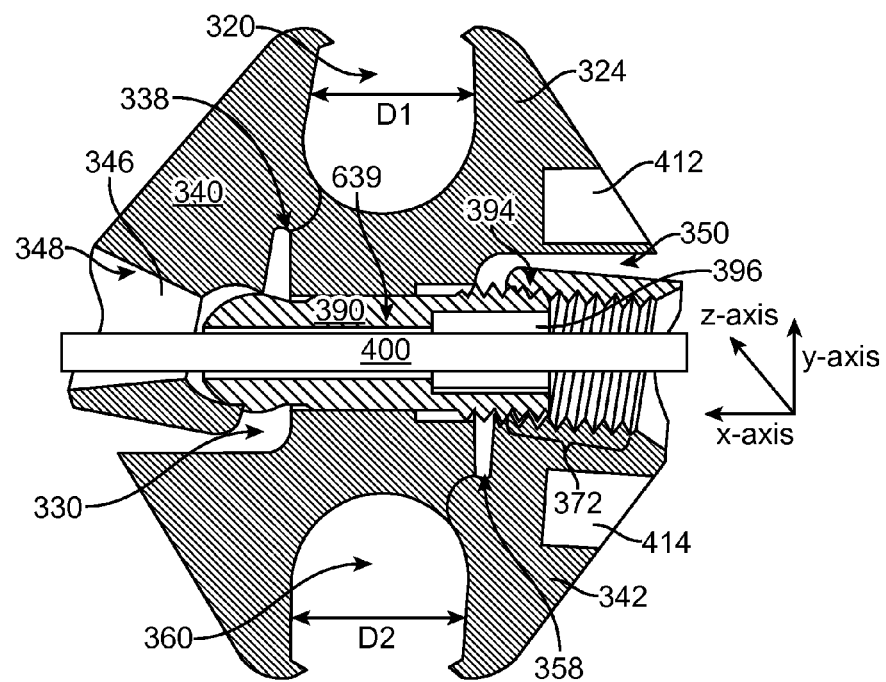
FIG. 10 is a cross-sectional view of one embodiment of the bilateral interspinous spacer showing the central screw 390 and the guide wire 400 passing through the threaded portion, the screw lumen, and the tapered hole 348.

As shown in FIG. 10, the first clamp section 320 and the second clamp section 360 include diameters D1 and D2, respectively, which may include a maximum and a minimum at which the diameters D1 and D2 may increase and decrease. The first slot 330 includes a first slot curvature 338 that acts as a pivot point to allow the first wing 340 to deform and angulate. The second slot 350 includes a second slot curvature 358 that acts as a pivot point to allow the second wing 342 to deform and angulate. Alternatively, the slot curvatures 338 and 358 include a hinge, whereby the slot curvature 338 that is hinge is coupled with the first clamp 322, the first wing 340, and the top portion 316 of the main body 310. The slot curvature 358 that is a hinge is coupled with the second clamp 364, the second wing 342, and the bottom portion 318 of the main body 310. The hinge is a type of bearing that connects the first clamp 322 and the first wing 340 with the top portion 316 of the main body and allows only a limited angle of rotation between them. As such, the first clamp 322 and the first wing 340 connected by the hinge rotate relative to the top portion 316 of the main body about a fixed axis of rotation. Likewise, the second clamp 364 and the second wing 342 connected by the hinge rotate relative to the bottom portion 318 of the main body about a fixed axis of rotation. The hinge may be made of flexible material such as a polymer or Nitinol, titanium, and like to allow for super elastic or plastic deformation.

As shown in FIG. 10, the threaded proximal portion 394 of the central screw 390 is tapered at an angle with respect to the longitudinal axis, in order to allow the second wing 342 to angulate or deform at an angle when the central screw 390 is rotated to concentrically engage the threaded section 372, thus becoming longitudinally movable by way of rotating the central screw 390. Alternatively, the threaded portion 372 of the second wing 342 may be tapered at an angle with respect to the longitudinal axis, such that the second wing 342 is able to angulate or deform when the central screw 390 is rotated. In one embodiment, both the threaded proximal portion 394 and the threaded portion 372 of the second wing 342 are tapered at an angle with respect to the longitudinal axis, such as to allow the second wing 342 to angulate or be deformed at an angle when the central screw 390 is rotated. Alternatively, the threaded portion 372 of the second wing 342 are tapered at the same angle with respect to the longitudinal axis, such as to allow the second wing 342 to angulate or be deformed at an angle when the central screw 390 is rotated.

Figure 11:
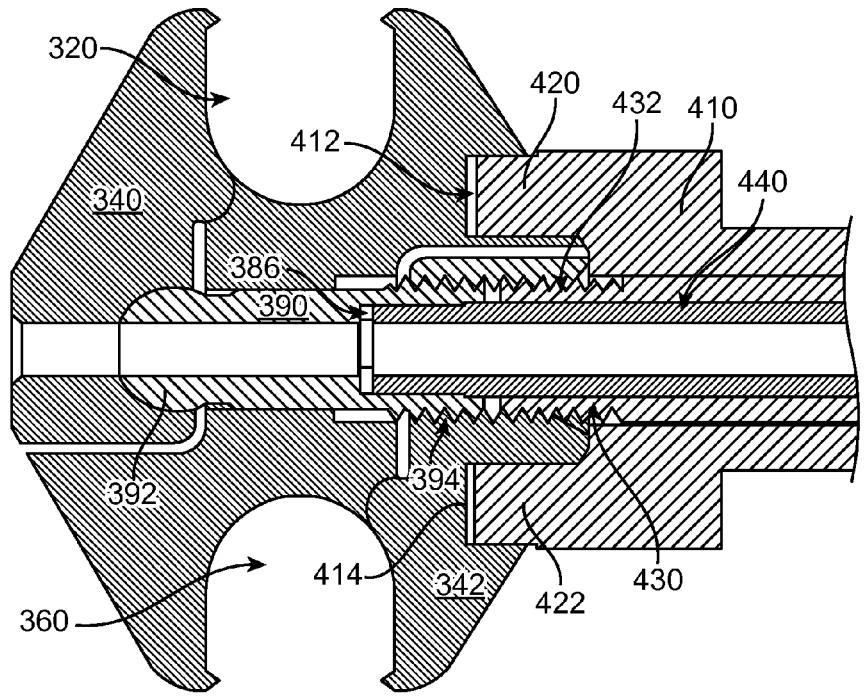
FIG. 11 is a cross-sectional view of one embodiment of the bilateral interspinous spacer showing the central screw 390 operably engaged with the screw driver 440 and the driver 410 operably engaged with the bilateral interspinous spacer.

As shown in FIG. 10, the central screw 390 includes a screw lumen 396 that extends substantially through the longitudinal axis of the central screw. The screw lumen 396 coaxially extends through the central tube 380 and the screw acceptor portion 386, as shown in FIG. 9. The wing lumen 346 in the first wing 340 includes a tapered edge 348 in the distal portion. A guide wire or K-wire 400 passes through the screw lumen 396 during delivery and through the wing lumen 346 and tapered edges 348, such that the K-wire does not get trapped or caught as the first wing 340 angulates or deforms. The proximal portion 314 includes a first driver lumen 412 and a second driver lumen 414 to accept a driver 410, as shown in FIG. 11. The first driver lumen 412 is positioned in the second clamp 324 of the first clamp section 320, while the second driver lumen 422 is positioned in the second wing 342.

The central screw 390, as shown in FIG. 11, operably engages the central longitudinal lumen 370, whereby the distal curved portion 392 abuts the curved section 378 and supports the first wing 340 during delivery of the bilateral clamping interspinous spacer 300. The driver 410 includes a first drive portion 420 and a second drive portion 422 to operably engage the first driver lumen 412 and the second driver lumen 414, respectively. During a 90 degree rotation of the bilateral clamping interspinous spacer 300, the driver 410 gains traction and adhesion to rotate the bilateral interspinous spacer 300 about the z-axis. Thus, both the first clamp section 320 and the second clamp section 360 are secured by the driver 410. The driver 410 includes a central drive lumen 430 and a drive threaded portion 432 that is coaxially located in the central portion of the driver 410. The drive threaded portion 432 concentrically engages the threaded portion 372 of the proximal portion 314 of the main body 310. The central drive lumen 430 allows for the passageway for a screwdriver 440 to operably engage the acceptor portion 386 of the central screw 390.

Figure 12:
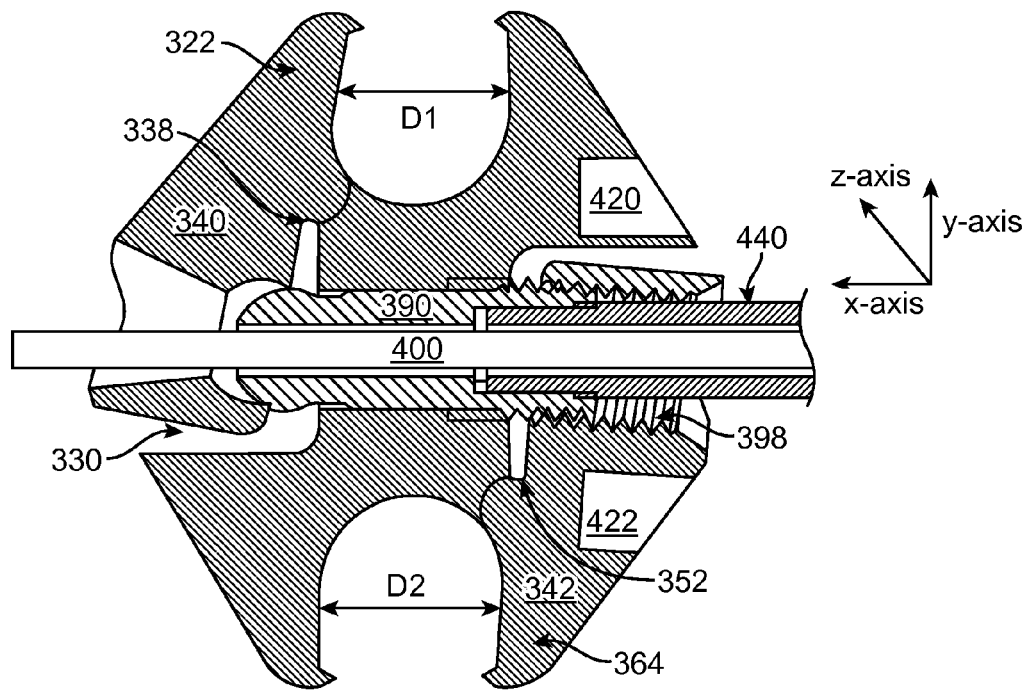
FIG. 12 is a cross-sectional view of one embodiment of the bilateral interspinous spacer showing the guide wire 400 passing through the screw lumen and the driver 440 longitudinally displacing the central screw 390 to deform the first wing 340 and the second wing 342.

As shown in FIG. 12, the driver 410 is removed from the first and second driver lumens 420 and 422, while the screwdriver 440 remains operably engaged with the central screw 390. The bilateral interspinous spacer 300 is deployed when an operator rotates the screwdriver 440 to longitudinally displace the central screw 390 and cause the first wing 340 to deform and angulate the first clamp 322 in the x-direction towards the proximal section 314 of the main body 310, while the second wing 342 deforms and angulates the second clamp 364 in the x-direction towards the distal section 312 of the main body 310. As such, the diameter D1 of the first clamp section is decreased by a proportional amount of the central screw's 390 longitudinal movement by the screwdriver 440, and the diameter D2 is also decreased by a proportional amount of the central screw 390 longitudinal movements by the screwdriver 440. The first slot curvature 338 and the second slot curvature 352 act as pivot points to allow the first wing 340 and the second wing 342 to deform and angulate, respectively. Accordingly, the first leg 352 and the second leg 354 of the second slot 350 increase in diameter when the second wing 342 deforms along the transverse axis of the main body 310. And the first leg 332 and the second leg 334 of the first slot 330 increase in diameter when the first wing 340 deforms along the transverse axis of the main body 310. In one embodiment, the central screw 390 may be coupled with a locking mechanism 398 as to prevent the backward movement of the central screw 390, which would decrease the diameter of the first and second slots 330 and 350 and increase diameters D1 and D2, as shown in FIG. 12. The locking mechanism 398 may be behind the central screw 390, which either may be a threaded ring or the threaded portion 372 of the central lumen 370. The threaded ring may be rotated in the central lumen 370 after the central screw 390 has deformed the first wing 340 and the second wing 342. The threaded portion 372 may include a threaded lock portion that maintains the central screw 390 from displacing longitudinally backwards once the first wing 340 and the second wing 342 is deformed and engaged on the spinous processes.

Figure 13:
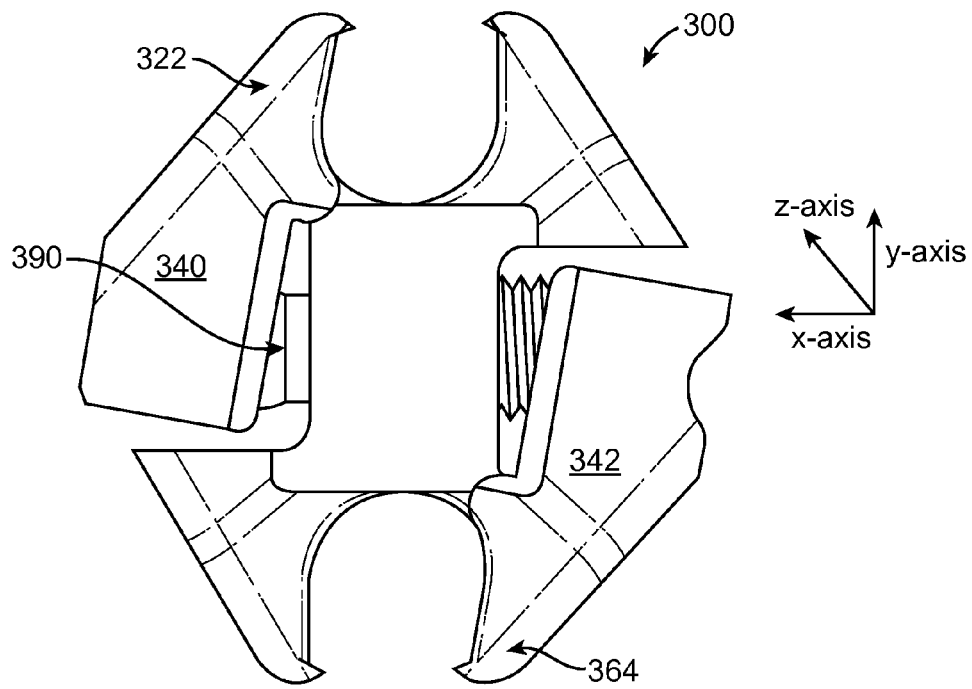
FIG. 13 is a perspective view of the exterior portion for one embodiment of the bilateral interspinous spacer showing the central screw 390 longitudinally displacing the first wing 340 and the second wing 342.

As shown in FIG. 13, when the central screw 390 is longitudinally displaced, the first wing 340 and the second wing 342 are angulated as to clamp the bilateral interspinous spacer 300 with the first clamp 322 and the second clamp 364 on the top and bottom portions, respectively. The first and second clamp sections clamp down and secure the bilateral interspinous spacer onto two spinous processes. The distance between the first and second clamp sections may be modified to secure the bilateral interspinous spacer between two spinous processes along the vertebrae section, including, but not limited to, the cervical, thoracic, lumbar, or sacral sections of the vertebrae.

Figure 14A:
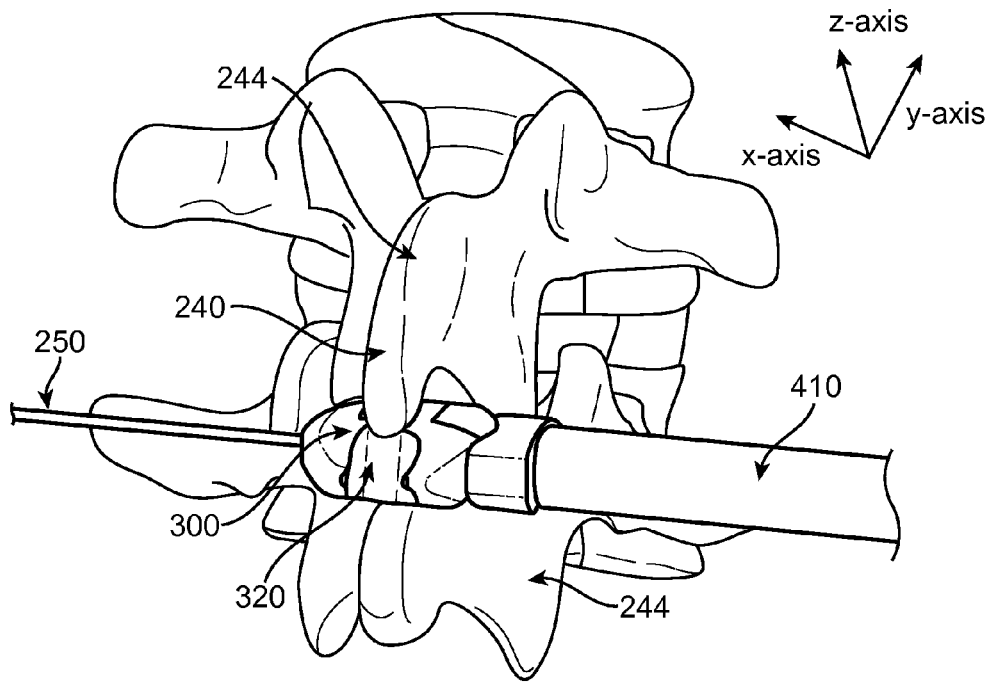
FIGS. 14A and 14B are perspective views of the vertebrae body and spinous process whereby the bilateral interspinous spacer is delivered and deployed between adjacent spinous processes in accordance with one embodiment.
Figure 14B:
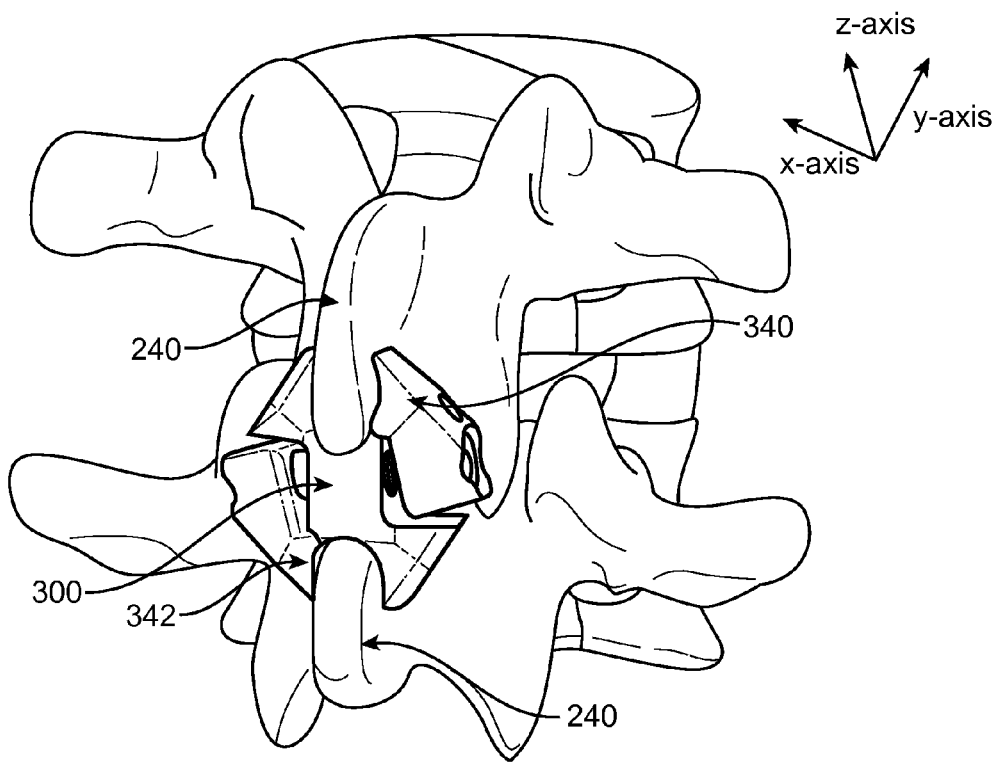

During delivery, the bilateral interspinous spacer 300 is delivered over a guide wire 250 or kirschner wire ("k-wire"), generally shown in FIG. 14A. The bilateral interspinous spacer 300 is placed between adjacent spinous processes 240 with the driver 410, whereby the first clamp section 320 is pointing towards the z-axis or away from the spine of the patient. Once the bilateral interspinous spacer 300 is between adjacent spinous processes 240, as shown in FIG. 14A, the bilateral interspinous spacer 300 is rotated 90 degrees by the driver 410 towards the y-axis or upwards towards the patient's head or feet in the y-axis direction, which provides a cam action to distend the vertebral bodies 244 and place the first clamp section 320 and the second clamp section 360 around the spinous process, as shown in FIG. 14B. Once the first clamp section 320 and the second clamp section 360 are around adjacent spinous processes, the hex driver 410 operably engages the central screw 390 and longitudinally displaces the central screw 390 to angulate or deform the first wing 340 and the second wing 342 onto the spinous processes.

Optionally, before the interspinous spacers 100 or 300 is deployed and implanted, provisional dilation of the spinous processes 240 is performed with cannulated conical screw or smooth semi conical shape dilators. During provisional dilation, the first dilator is inserted via the guide wire and cuts through the interspinous ligament using the sharp edges. The dilator distracts the spinous processes 240 if the dilator comes into contact with the spinous processes 240. Then, the first dilator is removed.

If the first dilator does not contact the spinous processes 240, a second dilator is inserted via the guide wire. The second dilator is larger than the first dilator and also cuts through the interspinous ligament. If necessary, several dilators, etc. can be used until one of the dilators contacts the spinous processes 240. The dilators can have slightly increasing outer diameters. For example, a 6 mm, an 8 mm, a 10 mm, a 12 mm, and a 14 mm dilator can be used. Contact between the dilator and the spinous processes 240 can be felt due to the tension provided between the spinous processes 240 by the super spinous ligament. Once the proper size is determined by the dilator, a distractor of an appropriate size can be selected.

As can be understood by one skilled in the art, the clamping interspinous spacer 100 and the bilateral interspinous spacer 300 and/or any of its components may have any size, shape, length, thickness, height, weight, or any other parameters. Such parameters may be selected by the surgeon (or other qualified professional) for performance of specific procedures. Further, the clamping interspinous spacer 100 and the bilateral interspinous spacer and/or any of its components may be manufactured from metal, plastic, synthetic material, or other suitable materials, or any combination thereof. Preferably, the interspinous spacers 100 and 300 are formed from polyether ether ketone (PEEK), which is a colorless organic polymer thermoplastic. Alternatively, the interspinous spacers 100 and 300 are formed from Nitinol or titanium, stainless steel, or other shape memory metal materials.

The embodiments disclosed herein seeks to minimize the number of component parts of the implant by using a flexible material such as PEEK plastic to create a "living" hinge within the body of the implant. The implant is clamped by activating the central screw that causes the clamp sections of the implant to pivot, close, and tighten against the spinous process. By using an oblong cross-section at the root of the jaws the implant can provide distraction of the spinous process by rotating it 90 degrees. This cam action helps restore original spinal column height while rotating the jaws into position around the spinous process. The implant can be designed with a single jaw or dual jaws which mimic the wing component of existing spinous process clamps.

The one piece body design with integral wings allows the creation of a sleek exterior which can be passed through soft tissue with minimal trauma. The implant may be delivered in a minimally invasive surgery (MIS) or an open surgery. The implant can be delivered over a K-wire which provides extra security and guides the implant into the propel position. Simply rotating the implant 90° positions the jaws between the spinous process and provides cam action to distend the vertebral bodies. The implant design is comprised of only the implant body and an activation screw minimizing any chance of movable parts coming loose and causing a complication in surgery. The delivery instrumentation is uncomplicated and comparable to the well proven interbody instrumentation consisting of an outer member secured to the implant and an internal means of rotating the actuation screw. The implant can be used alone or as a supplement to other spinal procedures.

While the invention has been described in connection with various embodiments, it will be understood that the invention is capable of further modifications. This application is intended to cover any variations, uses, or adaptations of the invention following, in general, the principles of the invention, and including such departures from the present disclosure as, within the known and customary practice within the art to which the invention pertains.

What is claimed is:

1. An interspinous process spacer, comprising:
   a main body including a first securing member extending from a top portion of the main body adapted for engagement with a first vertebra and a bottom portion of the main body adapted for engagement with a second vertebra;
   a first wing pivotably coupled to a distal portion of the main body and including a second securing member extending parallel to the first securing member to form a first clamp in a first position and nonparallel to the first securing member in a second position; and
   a screw positionable within the main body and including a distal end that positions the first wing between the first position wherein the first clamp includes a first diameter and the second position wherein the first clamp includes a second diameter,
   wherein the screw advances towards the distal portion to position the first wing from the first position to the second position,
   wherein the distal end of the screw includes a curved portion that engages a curved section of the first wing and the proximal end of the screw includes a threaded portion that engages a threaded bore in the main body, and
   wherein the first wing pivotably couples to the main body by a living hinge.

2. The interspinous process spacer of claim 1, wherein the first diameter is greater than a thickness of a spinous process of the first vertebra and the second diameter is less than the first diameter.

3. An interspinous spacer comprising:
   a main body, a clamp section, and a slot, wherein the main body includes a distal portion, a proximal portion, a top portion, and a bottom portion;
   the distal portion includes a first wing and the proximal portion includes a second wing, the bottom portion includes a curved segment, top portion includes the clamp section, wherein the clamp section includes a first clamp and a second clamp;

the first wing operably coupled to the slot and the first clamp, wherein the slot generally extends along transverse axis of the main body;

the slot includes a slot opening located at or near the bottom portion and a slot curvature at or near the top portion; and the clamp section and the curved segment enable the interspinous spacer to be secured between two spinous processes such that one spinous process rests in the curved segment and another spinous process rests in the clamp section;

wherein the main body includes a central longitudinal lumen extending along at least a portion of a longitudinal axis of the main body, wherein the central longitudinal lumen includes a threaded section, a curved section, a central tube, and a central screw, the threaded section extends from the proximal portion and through the central portion of the main body to the slot;

the threaded section includes an opening on the proximal portion of the second wing;

the curved section longitudinally extends from the slot to the distal portion and the first wing;

the central screw includes a distal curved section, a central threaded portion, and a screw lumen;

the distal curved section operably engages the curved section of the first wing, such as to support the first wing during delivery and displace the first wing during longitudinal movement of the central screw;

the central threaded portion operably engages the threaded section.

4. The interspinous spacer of claim 3, wherein the clamp section includes a diameter Dc and the first clamp and the second clamp include inward facing hooks on the distal end of the first clamp and the second clamp.

5. The interspinous spacer of claim 3, wherein the slot extends from top portion to the bottom portion.

6. The interspinous spacer of claim 3, wherein the distal curved section includes a smaller diameter than the central threaded portion, such that the central screw may rotatably engage with the threaded portion of the central longitudinal lumen.

* * * * *